(12) United States Patent
Betser et al.

(10) Patent No.: US 11,712,356 B2
(45) Date of Patent: Aug. 1, 2023

(54) EXPANDED DEVICE

(71) Applicant: EPITOMEE MEDICAL LTD., Caesarea (IL)

(72) Inventors: Nir Betser, Yehud (IL); Valery Artmanov, Ashdod (IL); Ran Kapri, Mazkeret-Batya (IL)

(73) Assignee: Epitomee Medical LTD, Caesarea (IL)

( * ) Notice: Subject to any disclaimer, the term of this patent is extended or adjusted under 35 U.S.C. 154(b) by 996 days.

(21) Appl. No.: 16/439,865

(22) Filed: Jun. 13, 2019

(65) Prior Publication Data

US 2019/0307593 A1    Oct. 10, 2019

Related U.S. Application Data

(63) Continuation of application No. 14/405,836, filed as application No. PCT/IL2013/050490 on Jun. 6, 2013, now Pat. No. 10,507,127.

(60) Provisional application No. 61/656,788, filed on Jun. 7, 2012.

(51) Int. Cl.
    *A61F 5/00*     (2006.01)
    *A61L 15/60*     (2006.01)
    *A61L 31/14*     (2006.01)

(52) U.S. Cl.
    CPC ............ *A61F 5/0036* (2013.01); *A61L 15/60* (2013.01); *A61L 31/148* (2013.01)

(58) Field of Classification Search
    CPC ........ A61F 5/0036; A61F 5/003; A61L 15/60; A61L 31/148
See application file for complete search history.

(56) References Cited

U.S. PATENT DOCUMENTS

| | | | |
|---|---|---|---|
| 2,464,693 | A | 3/1949 | Kirk |
| 2,470,665 | A | 5/1949 | Stiehl |
| 3,584,631 | A | 6/1971 | Halter et al. |
| 3,630,114 | A | 12/1971 | Bunting, Jr. et al. |
| 3,674,014 | A | 7/1972 | Tillander |
| 3,774,596 | A | 11/1973 | Cook |
| 3,786,813 | A | 1/1974 | Michaels |
| 3,840,009 | A | 10/1974 | Michaels et al. |
| 3,901,232 | A | 8/1975 | Michaels et al. |
| 3,911,098 | A | 10/1975 | Capozza |
| 4,027,676 | A | 6/1977 | Mattei |
| 4,055,178 | A | 10/1977 | Harrigan |
| 4,133,315 | A | 1/1979 | Berman et al. |
| 4,140,755 | A | 2/1979 | Sheth et al. |

(Continued)

FOREIGN PATENT DOCUMENTS

| | | |
|---|---|---|
| DE | 10304614 | 8/2004 |
| EP | 0103481 | 3/1984 |

(Continued)

OTHER PUBLICATIONS

Rattner, et al, Introduction to Materials Science, Biomaterials Science, 2004.

(Continued)

*Primary Examiner* — Steven O Douglas
(74) *Attorney, Agent, or Firm* — Paul D. Bianco; Gary S. Winer; Fleit Intellectual Property Law (57) ABSTRACT

A folded expandable gastro-retentive device and its uses in human medical care include, inter alia, appetite suppression in a subject in need thereof. The expanded device can be included in kits.

20 Claims, 5 Drawing Sheets

(56) References Cited

U.S. PATENT DOCUMENTS

| | | |
|---|---|---|
| 4,142,526 A | 3/1979 | Zaffaroni et al. |
| 4,167,558 A | 9/1979 | Sheth et al. |
| 4,203,439 A | 5/1980 | Theeuwes |
| 4,207,890 A | 6/1980 | Mamajek et al. |
| 4,236,521 A | 12/1980 | Lauterjung |
| 4,246,893 A | 1/1981 | Berson |
| 4,308,250 A | 12/1981 | Griffin et al. |
| 4,311,146 A | 1/1982 | Wonder |
| 4,416,267 A | 11/1983 | Garren et al. |
| 4,447,227 A | 5/1984 | Kotsanis |
| 4,485,805 A | 12/1984 | Foster, Jr. |
| 4,501,264 A | 2/1985 | Rockey |
| 4,546,143 A | 10/1985 | Weil et al. |
| 4,607,618 A | 8/1986 | Angelchik |
| 4,692,152 A | 9/1987 | Emde |
| 4,694,827 A | 9/1987 | Weiner et al. |
| 4,723,547 A | 2/1988 | Kullas et al. |
| 4,739,758 A | 4/1988 | Lai et al. |
| 4,753,976 A | 6/1988 | Yoshioka et al. |
| 4,767,627 A | 8/1988 | Caldwell et al. |
| 4,790,429 A | 12/1988 | Fukushima |
| 4,812,315 A | 3/1989 | Tarabishi |
| 4,878,905 A | 11/1989 | Blass |
| 4,899,747 A | 2/1990 | Garren et al. |
| 4,925,446 A | 5/1990 | Garay et al. |
| 4,968,294 A | 11/1990 | Salama |
| 4,984,564 A | 1/1991 | Yuen |
| 5,041,364 A | 8/1991 | Dickerson et al. |
| 5,084,061 A | 1/1992 | Gau et al. |
| 5,129,915 A | 7/1992 | Cantenys |
| 5,167,626 A | 12/1992 | Casper |
| 5,206,030 A | 4/1993 | Wheatley et al. |
| 5,234,454 A | 8/1993 | Bangs |
| 5,259,399 A | 11/1993 | Brown |
| 5,443,505 A | 8/1995 | Wong et al. |
| 5,520,609 A | 5/1996 | Moll et al. |
| 5,558,642 A | 9/1996 | Schweich, Jr. et al. |
| 5,649,978 A | 7/1997 | Samson |
| 5,738,629 A | 4/1998 | Moll et al. |
| 5,750,585 A | 5/1998 | Park et al. |
| 5,770,181 A | 6/1998 | Kirkland |
| 5,783,212 A | 7/1998 | Fassihi et al. |
| 5,836,871 A | 11/1998 | Wallace et al. |
| 5,893,826 A | 4/1999 | Salama |
| 5,972,369 A | 10/1999 | Roorda et al. |
| 5,989,590 A | 11/1999 | Wong et al. |
| 5,993,473 A | 11/1999 | Chan et al. |
| 6,079,871 A | 6/2000 | Jonas et al. |
| 6,120,803 A | 9/2000 | Wong et al. |
| 6,261,601 B1 | 7/2001 | Talwar et al. |
| 6,271,278 B1 | 8/2001 | Park et al. |
| 6,287,332 B1 | 9/2001 | Bolz et al. |
| 6,454,785 B2 | 9/2002 | De Hoyos Garza |
| 6,503,264 B1 | 1/2003 | Birk |
| 6,517,559 B1 | 2/2003 | O'Connell |
| 6,517,659 B1 | 2/2003 | VanderWerf et al. |
| 6,579,301 B1 | 6/2003 | Bales et al. |
| 6,579,310 B1 | 6/2003 | Cox et al. |
| 6,605,037 B1 | 8/2003 | Moll et al. |
| 6,675,809 B2 | 1/2004 | Stack et al. |
| 6,726,920 B1 | 4/2004 | Theeuwes et al. |
| 6,733,512 B2 | 5/2004 | McGhan |
| 6,755,869 B2 | 6/2004 | Geltz |
| 6,797,283 B1 | 9/2004 | Edgren et al. |
| 6,833,488 B2 | 12/2004 | Bucevschi et al. |
| 6,845,776 B2 | 1/2005 | Stack et al. |
| 6,981,980 B2 | 1/2006 | Sampson et al. |
| 7,009,634 B2 | 3/2006 | Iddan et al. |
| 7,033,373 B2 | 4/2006 | de la Torre et al. |
| 7,052,488 B2 | 5/2006 | Uhland |
| 7,056,305 B2 | 6/2006 | Garza Alvarez |
| 7,066,945 B2 | 6/2006 | Hashiba et al. |
| 7,111,627 B2 | 9/2006 | Stack et al. |
| 7,112,186 B2 | 9/2006 | Shah |
| 7,335,210 B2 | 2/2008 | Smit |
| 7,632,291 B2 | 12/2009 | Stephens et al. |
| 7,674,396 B2 | 3/2010 | Sterling et al. |
| 7,699,863 B2 | 4/2010 | Marco |
| 7,699,883 B2 | 4/2010 | Douglas |
| 7,785,291 B2 | 8/2010 | Marco et al. |
| 7,879,355 B2 | 2/2011 | Sterling et al. |
| 7,931,693 B2 | 4/2011 | Binmoeller |
| 8,267,888 B2 | 9/2012 | Marco et al. |
| 8,292,911 B2 | 10/2012 | Brister et al. |
| 8,647,358 B2 | 2/2014 | Brister et al. |
| 8,740,927 B2 | 6/2014 | Brister et al. |
| 8,845,673 B2 | 9/2014 | Marco et al. |
| 8,858,496 B2 | 10/2014 | Marco et al. |
| 8,864,784 B2 | 10/2014 | Marco et al. |
| 8,992,561 B2 | 3/2015 | Brister et al. |
| 9,119,793 B1 | 9/2015 | Bakan et al. |
| 2003/0040804 A1 | 2/2003 | Stack et al. |
| 2003/0040808 A1 | 2/2003 | Stack et al. |
| 2003/0109935 A1 | 6/2003 | Geitz |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0212452 A1 | 11/2003 | Zadno-Azizi et al. |
| 2004/0129186 A1 | 7/2004 | Curiger |
| 2004/0143342 A1 | 7/2004 | Stack et al. |
| 2004/0186502 A1 | 9/2004 | Sampson et al. |
| 2004/0192582 A1 | 9/2004 | Burnett et al. |
| 2004/0219186 A1 | 11/2004 | Ayres |
| 2005/0216074 A1 | 9/2005 | Sahatjian et al. |
| 2006/0018948 A1 | 1/2006 | Guire et al. |
| 2006/0025799 A1 | 2/2006 | Basu |
| 2006/0058829 A1 | 3/2006 | Sampson et al. |
| 2006/0111632 A1 | 5/2006 | Chen |
| 2006/0111777 A1 | 5/2006 | Chen |
| 2006/0155259 A1 | 7/2006 | MacLay |
| 2006/0178726 A1 | 8/2006 | Douglas |
| 2006/0222681 A1 | 10/2006 | Richard |
| 2006/0282107 A1 | 12/2006 | Hashiba et al. |
| 2007/0078476 A1 | 4/2007 | Hull et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0104754 A1 | 5/2007 | Sterling et al. |
| 2007/0104755 A1* | 5/2007 | Sterling ............... A61F 5/0036 424/423 |
| 2007/0106372 A1 | 5/2007 | Osborne et al. |
| 2007/0118168 A1 | 5/2007 | Lointier et al. |
| 2007/0135829 A1 | 6/2007 | Paganon |
| 2007/0224234 A1 | 9/2007 | Steckel et al. |
| 2007/0249900 A1 | 10/2007 | Wilson et al. |
| 2007/0250102 A1 | 10/2007 | Makower et al. |
| 2007/0250103 A1 | 10/2007 | Makower et al. |
| 2007/0265709 A1 | 11/2007 | Rajan et al. |
| 2007/0293716 A1 | 12/2007 | Baker et al. |
| 2008/0107732 A1 | 5/2008 | Dharmadhikari et al. |
| 2008/0206145 A1 | 8/2008 | Afargan et al. |
| 2008/0208356 A1 | 8/2008 | Stack |
| 2008/0255587 A1 | 10/2008 | Cully et al. |
| 2008/0269797 A1 | 10/2008 | Stack et al. |
| 2009/0035367 A1 | 2/2009 | Mintchev et al. |
| 2009/0098198 A1* | 4/2009 | Rousso ............... A61K 9/4808 424/725 |
| 2009/0130158 A1 | 5/2009 | Dujardin et al. |
| 2009/0177215 A1 | 7/2009 | Stack et al. |
| 2009/0182424 A1 | 7/2009 | Marco |
| 2009/0299487 A1 | 12/2009 | Stack et al. |
| 2009/0304753 A1 | 12/2009 | Tsabari et al. |
| 2009/0304768 A1 | 12/2009 | Lapidot et al. |
| 2009/0318649 A1 | 12/2009 | Bucevschi |
| 2010/0129445 A1 | 5/2010 | Asmussen et al. |
| 2011/0015665 A1 | 1/2011 | Marco |
| 2011/0015666 A1 | 1/2011 | Marco |
| 2011/0022072 A1 | 1/2011 | Marco |
| 2011/0040318 A1 | 2/2011 | Marco et al. |
| 2011/0066175 A1 | 3/2011 | Gross |

(56) References Cited

U.S. PATENT DOCUMENTS

| | | | | |
|---|---|---|---|---|
| 2011/0112383 | A1* | 5/2011 | Voss | A61F 5/003 600/302 |
| 2013/0218190 | A1* | 8/2013 | Gaur | A61F 5/0043 606/192 |
| 2018/0250226 | A1 | 9/2018 | Betser et al. | |

FOREIGN PATENT DOCUMENTS

| | | | |
|---|---|---|---|
| EP | 1124534 | A1 | 8/2001 |
| EP | 1732522 | A2 | 12/2006 |
| JP | H03500258 | A | 1/1991 |
| JP | 2006522643 | A | 10/2006 |
| WO | 90/00376 | | 1/1990 |
| WO | 99025418 | | 5/1999 |
| WO | 00/25742 | A1 | 5/2000 |
| WO | 02/00213 | A1 | 1/2002 |
| WO | 02040081 | | 5/2002 |
| WO | 02091961 | | 11/2002 |
| WO | 03015745 | | 2/2003 |
| WO | 03017882 | | 3/2003 |
| WO | 03028477 | | 4/2003 |
| WO | 04064680 | | 8/2004 |
| WO | 04084763 | | 10/2004 |
| WO | 05018417 | | 3/2005 |
| WO | 05039458 | | 5/2005 |
| WO | 05082296 | | 9/2005 |
| WO | 05097012 | | 10/2005 |
| WO | 2005/101983 | A2 | 11/2005 |
| WO | 05101983 | | 11/2005 |
| WO | 05120363 | | 12/2005 |
| WO | 06020929 | | 2/2006 |
| WO | 06044640 | | 4/2006 |
| WO | 06047882 | | 5/2006 |
| WO | 06055839 | | 5/2006 |
| WO | 06063593 | | 6/2006 |
| WO | 06072948 | | 7/2006 |
| WO | 07017842 | | 2/2007 |
| WO | 07083309 | | 7/2007 |
| WO | 07084724 | | 7/2007 |
| WO | 07093999 | | 8/2007 |
| WO | 2007/109904 | | 10/2007 |
| WO | 07115169 | | 10/2007 |
| WO | 07136735 | | 11/2007 |
| WO | 2009/086119 | | 7/2009 |
| WO | 2010/045477 | | 4/2010 |

OTHER PUBLICATIONS

Japanese Office Action Translation dated Mar. 29, 2012 for Japanese Patent No. 2009-511077.
International Search Report published Apr. 30, 2009 for PCT/IL06/0276 filed Mar. 1, 2006.
Written Opinion published Mar. 20, 2009 for PCT/IL06/0276 filed Mar. 1, 2006.
International Preliminary Report on Patentability published Mar. 24, 2009 for PCT/IL06/0276 filed Mar. 1, 2006.
Klucel (TM) hydroxypropylcellulose—Physical and chemical properties, Ashland Inc., 2017, 24 pages.
International Search Report published Feb. 28, 2008 for PCT/US07/11882 filed May 18, 2007 (claiming priority to U.S. Appl. No. 11/788,574).
Written Opinion published Nov. 18, 2008 for PCT/US07/11882 filed May 18, 2007 (claiming priority to U.S. Appl. No. 11/788,574).
International Preliminary Report on Patentability published Nov. 18, 2008 for PCT/US07/11882 filed May 18, 2007 (claiming priority to U.S. Appl. No. 11/788,574).
International Search Report dated Dec. 2, 2013 for PCT/IL2013/050490.
Written Opinion dated Dec. 2, 2013 for PCT/IL2013/050490, Dec. 7, 2014 for PCT/IL2013/050490.
International Preliminary Examination Report dated Dec. 9, 2014 for PCT/IL2013/050490.

* cited by examiner

EXPANDED DEVICE

FIELD

This invention relates to an expanded device and us uses in human medical care, which include, inter alia, appetite suppression in a subject in need thereof and kits comprising thereof.

BACKGROUND

The prevalence of overweight and obesity is increasing at an alarming rate, and obesity has become one of the most important avoidable risk factors for morbidity and mortality. Based on a healthy body mass index (BMI), about one-third of the US adults are considered obese (BMI≥30 kg/m$^2$) and an additional third is overweight (BMI≥25 kg/m$^2$). Due to the medical and psychosocial impact of being overweight, as well as the difficulty in making sustained improvements in diet and physical activity, patients often turn to over-the-counter (OTC) proprietary weight-loss products containing single or multiple dietary supplements (e.g., herbs, vitamins, minerals, amino-acids).

Another approach to induce weight loss is to increase satiation and reduce the urge for food intake by administering devices that swell in the stomach and after residence time therein are evacuated through the GI (gastrointestinal tract). Such commercial products are: "Formoline" (Certmedica International GMBH), "CM3" (Easyway GMBH), "The Fill Pill" (Holms enterprises Inc.), "Zalak B" (Arcadia Herba Ltd.), "Avantrx" (Biosyntrx, Inc.), "PREE" (Wellosophy Corp.).

The efficiency of most of these known devices depends on parameters such as: extent of swellability of the device in situ, device size and/or specific shape to ensure device residence in the stomach for minimum time period, strength of the swelled device to withstand excessive gastric pressures, strength of the device to stimulate the mechanoreceptors on the stomach wall, ability to encase the device into a swallowable size capsule, ability of the device to create large and effective volume in the stomach, ability of the device size and shape to imitate stomach functioning to the existing of solid parts and to delay the content emptying, compatibility with dynamic gastric changes (pH, conductivity, water content, foods and drugs), capability of the device to decline and pass the pylorus (a barrier between the gastric and intestine) after residence time in the stomach, degradation in the intestine to avoid GI obstructions.

General Description

The present invention provides a device comprising at least one compartment having an external biodegradable film enclosing a composition comprising at least one gel forming compound, wherein said at least one compartment is encased within a gastric degradable swallowable size capsule.

In some embodiments, said composition further comprises at least one gas forming compound.

The term "compartment" should be understood to encompass a separate division or section having a space enclosed by said external biodegradable film. Said compartment may be in any shape or form suitable for the purposes of the device of the invention. Furthermore, a device of the invention may include one or more of said compartments, which in some embodiments may be interconnected to one another or separated. Said compartment of the invention has an initial volume (i.e. its volume when encased (for example folded) within said swallowable size capsule, is between 0.13 cm$^3$-2.4 cm$^3$, which is increased to an expanded volume upon its use in the stomach (up to 150 cm$^3$).

In some embodiments, said at least one compartment has a total filling volume at the expanded state (defined at 37° C. for 1 hour) of at least 1 cm$^3$. In further embodiments, said compartment has a filling volume of about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150 cm$^3$. In other embodiments, said compartment has a filling volume of between about 3 cm$^3$ to about 150 cm$^3$. In other embodiments, said compartment has a filling volume of between about 3 cm$^3$ to about 70 cm$^3$. In yet other embodiments, said compartment has a filling volume of between about 8 cm$^3$ to about 30 cm$^3$. In further embodiments, said compartment has a filling volume of between about 40 cm$^3$ to about 70 cm$^3$. In some further embodiments, said compartment has a filling volume of between about 1 cm$^3$ to about 15 cm$^3$. In yet further embodiments said compartment has a filling volume of between about 80 cm$^3$ to about 150 cm$^3$.

In other embodiments, said single compartment has dimensions of between about 15 to about 95 mm in max external length and between about 5 to 45 mm in max external width. In yet other embodiments, said compartment has a max external elongation of about 15, 16, 17, 18, 19, 20, 25, 35, 45, 55, 65, 75, 85, 95 mm and max external wideness of about 5, 6, 7, 8, 9, 10, 15, 20, 25, 30, 35, 40, 45 mm. In yet some other embodiments, said compartment has dimensions of between about 50 to about 75 mm in max external length and between about 12 to about 25 mm in max external width. In yet further embodiments, said compartment has a max external elongation of about 50, 55, 60, 65, 70, 75 mm and max external wideness of about 12, 13, 14, 15, 16, 17, 18, 19, 20, 21, 22, 23, 24, 25 mm.

In some other embodiments, said device of the invention has a mass of between about 1 to about 150 gr at the expanded state (defined at 37° C. for 1 hour). In yet other embodiments, said device of the invention has a mass of about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, 120, 125, 130, 135, 140, 145, 150 gr at the expanded state. In further embodiments, said device of the invention has a mass of between about 8 to about 35 gr at the expanded state. In yet further embodiments, said device of the invention has a mass of about 8, 9, 10, 11, 12, 13, 14, 15, 20, 25, 30, 35 gr at the expanded state.

The term "external biodegradable film" (also referred herein as "envelope film") should be understood to encompass a single or multilayered film made of biodegradable material or a combination of materials forming the perimeters (walls) of said compartment of a device of the invention and enclosing within said compartment said composition comprising said at least one gel and/or gas forming compound.

When referring to a "biodegradable film" it should be understood to mean that said film is degraded or film's properties are deteriorated when exposed to biological environment (i.e. in a biological system, or similar in vitro environment simulating conditions of such biological system, such as gastric tract of a treated individual). In some embodiments, degradation or deterioration of said film is manifested by the reduction in one or more of film's physical properties such as for example film integrity, tensile strength and/or elasticity of said film.

In some embodiments, said external biodegradable film has a thickness of less than 70 microns. In further embodiments, said external biodegradable film has a thickness of between about 3 to about 60 microns. In yet other embodiments, said external biodegradable film has a thickness of about 3, 4, 5, 6, 7, 8, 9, 10, 15, 20, 25, 30, 35, 40, 45, 50, 55, 60 microns. In further embodiments, said external biodegradable film has a thickness of between about 10 to about 30 microns. In yet other embodiments, said external biodegradable film has a thickness of about 10, 11, 12, 13, 14, 15, 16, 17, 18, 19, 20, 21, 22, 23, 24, 25, 26, 27, 28, 29, 30 microns.

In other embodiments, said external biodegradable film is a multilayered film (i.e. formed from more than one layer). In some embodiments, said multilayered film has at least two different layers. In other embodiments, said multilayered film has at least three different layers.

In yet other embodiments, said external biodegradable film is enterically degradable (i.e. its properties are deteriorated, reduction in one or more of tensile strength and/or elasticity, upon exposure to a biological system or its similar in vitro environment, for example in the intestine).

In further embodiments, said external biodegradable film is formed by any method known in the art, including but not limited to: blowing, casting, extrusion, coating, lamination and any combination thereof.

In yet further embodiments, two layers of said external biodegradable film are connected by gluing, welding, suturing, sealing, pressing or any other method known in the art to form a closed "pocket" enclosing said at least one gel and/or gas forming compound, defined above and below as the compartment.

In some embodiment, said external biodegradable film of a compartment of a device of the invention is foldable in a manner that enables its enclosure in a swallowable capsule (i.e. when folding the external biodegradable film or said compartment made of film, said film is not brittle or suffers any breakage).

Thus, as defined herein above and below, a capsule of a device of the invention, i.e. a swallowable size capsule, encases said at least one compartment in a folded or non-expanded form.

When administered to a patient in need thereof, said capsule is being swallowed orally and delivered to the stomach. Upon its reach to the stomach (see FIG. 1), said encasement of said capsule is degraded exposing said at least one compartment to the stomach fluids (de-capsulation of said compartment).

In further embodiments when said device of the invention reaches the stomach (i.e. in situ), said external biodegradable film of said at least one compartment allows the penetration of liquid into said compartment, thereby forming a gel and/or gas within said compartment and at least partially filling (expanding) the volume of said compartment. Thus, upon formation of a gel and/or gas in said at least one compartment, said compartment is defined to be in its open or expanded form, substantially to said full filling volume of said at least one compartment. In some embodiments, said at least one compartment is maintained in situ (in the stomach) in its expanded form (i.e. maintains its substantially full filling volume) for a period of at least 0.5 hrs. In other embodiments, said at least one compartment is maintained to situ in its expanded form for a period of 3 hrs to 8 hrs. In further embodiments, said at least one compartment is maintained in situ in its expanded form for a period over 8 hrs. In other embodiments, said at least one compartment is maintained in situ and evacuates from the stomach after less than about 24 hrs from administration, leave the stomach clean from device and ready for next administration. In other embodiments, said at least one compartment is maintained in situ between about 1 to about 30 days.

In some embodiments, said film of said at least one compartment is being gradually degraded and disintegrated (i.e. said envelope film is being gradually degraded and disintegrated so that compartment shape and size is reduced gradually). It is noted that degradation of said film could be achieved by any process including: mechanical degradation (such as gastric/intestine pulses), chemical degradation (such as acidic/basic pH) or biological degradation (such as enzymatic activity). In some further embodiments degradation of said at least one compartment is achieved after residing in the stomach for a period of between about 0.5 hrs to 30 days.

Figure 1:
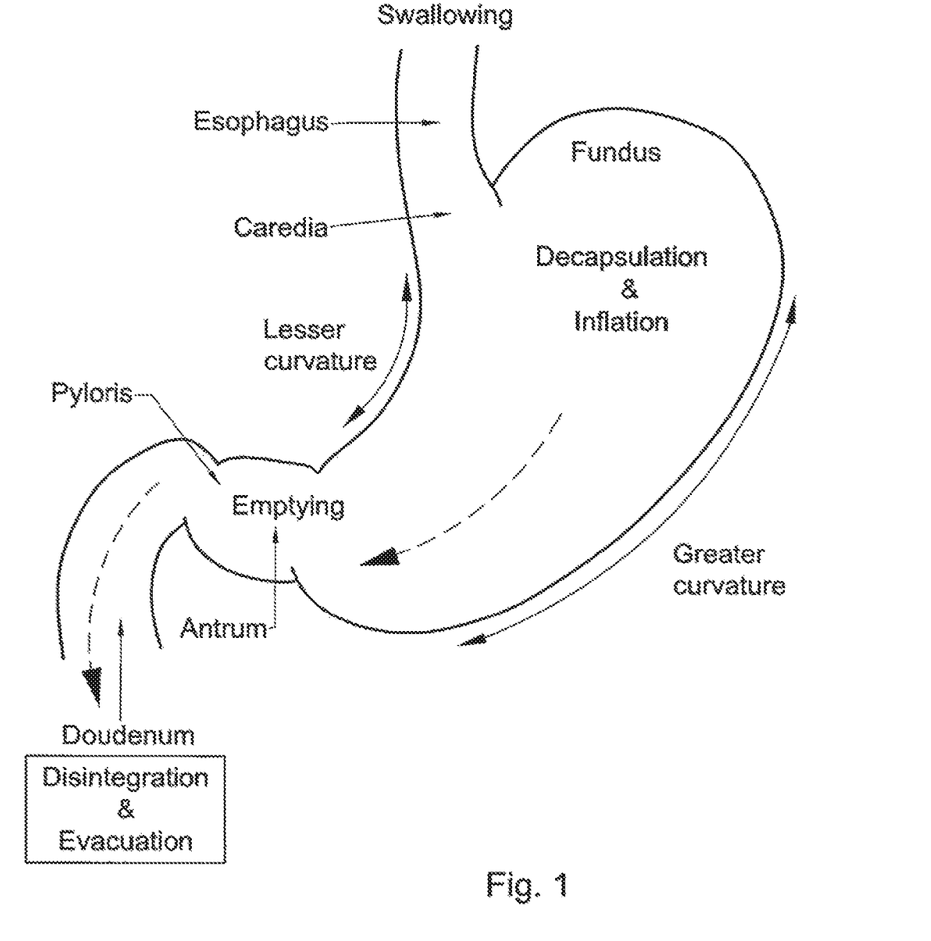
FIG. 1 is a schematic illustration depicting the route of said device of the invention within the stomach until evacuation to the intestine.

FIG. 1 shows the route of a device of the invention in the body. After swallowing, said device reaches the stomach, wherein said external capsule is degraded, exposing folded at least one compartment to the stomach's environment. Said folded compartment unfolds while expanding upon its contact with the stomach's fluids (expansion of said at least one compartment is achieved upon liquid reaching said composition comprising at least one gel or/and gas forming compound in said at least one compartment, thereby forming a gel/gas), and eventually reaches a 3-dimensional structure with an expanded volume. After a predetermined residence time in the stomach, said at least one compartment declines and is evacuated through the pylorus into the intestine, where it is degraded and then evacuated from the body. In some embodiments the degradation of the external film of said at least one compartment may be initiated or occur in the stomach.

In some embodiments, said external biodegradable film comprises at least two layers, each of which may be formed from at least one polymer. In other embodiments each layer may be formed from at least two polymers.

In some embodiment of the invention, said first layer of an external biodegradable film of the invention is hydrophilic. In some embodiments said second layer of said external biodegradable film is an enteric layer (i.e. substantially maintains its properties under gastric conditions however degradable under intestine conditions).

In some embodiments of the invention, said external biodegradable film comprises at least one layer. In some embodiments said at least one layer is an enteric layer or non-enteric layer.

In further embodiments, said external biodegradable film has a tensile strength under dry conditions of between about 10 to about 80 MPa. In yet further embodiments, said external biodegradable film has a tensile strength under dry conditions of about 10, 11, 12, 13, 14, 15, 16, 17, 18, 19, 20, 25, 30, 35, 40, 45, 50, 55, 60, 65, 70, 75, 80 MPa. In other embodiments, said external biodegradable film has a tensile strength under dry conditions of between about 20 to 30 MPa. In yet other embodiments, said external biodegradable film has a tensile strength under dry conditions of about 20, 21, 22, 23, 24, 25, 26, 27, 28, 29, 30 MPa.

In some embodiments, said external biodegradable film has a tensile strength under wet conditions of between about 4 to about 40 MPa. In some other embodiments, said external biodegradable film has a tensile strength under wet conditions of about 4, 5, 6, 7, 8, 9, 10, 11, 12, 13, 14, 15, 16, 17, 18, 19, 20, 22, 23, 24, 25, 30, 35, 40 MPa. In yet some embodiments, said external biodegradable film has a tensile strength under wet conditions of between about 6 to about 12 MPa. In yet some other embodiments, said external biodegradable film has a tensile strength under wet conditions of about 6, 7, 8, 9, 10, 11, 12 MPa.

In further embodiments, said external biodegradable film has elasticity (elongation at break) under wet conditions of between about 10% to about 100% elongation. In yet further embodiments, said external biodegradable film has elasticity of about 10, 11, 12, 13, 14, 15, 20, 25, 30, 35, 40, 45, 50, 55, 60, 65, 70, 75, 80, 85, 90, 95, 100% elongation. In other embodiments said external biodegradable film has elasticity (elongation at break) under wet conditions of between about 10% to about 45% elongation. In other embodiments, said external biodegradable film has elasticity under wet conditions of between about 20% to about 35% elongation. In yet other embodiments, said external biodegradable film has elasticity under wet conditions of about 20, 21, 22, 23, 24, 25, 26, 27, 28, 29, 30, 31, 32, 33, 34, 35% elongation.

In some embodiments, when measured under Gastric Fluid Stimuli (GFS pH=1.2), reduction in elasticity and tensile strength was observed after about 5 hrs. In other embodiments, when measured under Intestine Fluid Stimuli (IFS pH=6.5), reduction in elasticity and tensile strength was after less than 2 hrs. In other embodiments, resilience time of said at least one compartment in the stomach is at least 0.5 h. In other embodiments, residence time of said at least one compartment in the stomach is less than 24 hrs. In further embodiments, residence time of said at least one compartment in the stomach (i.e. the time the device is maintained in the stomach in any form, either folded or expanded, before evacuation) is between about 0.5 hrs to about 30 days.

In some embodiments, said external biodegradable film comprises at least one mechanically or chemically formed aperture. In other embodiments said compartment comprises at least one mechanically or chemically formed aperture. Said aperture may be macroscopic or microscopic. In further embodiments, said external biodegradable film is free of apertures.

The term "gel forming compound" is meant to encompass any compound that is capable of absorbing any type of liquid(s) in contact therewith, thereby forming a three dimensional gel matrix (i.e. a three dimensional formation of the polymer). In some embodiments said gel forming compound is a polymer. In some embodiments said gel forming compound may be charged (i.e. charged gel forming compound) or neutral.

In some embodiments the gel matrix can be cross-linked. The term includes compounds from any source, being a natural source (wherein said compound forms a biopolymer), a synthetic source or a semi-synthetic source, and any combinations thereof.

Without being bound by theory, the molecular weight of the gel forming compounds and the degree of cross-linking within the gel matrix are the major factors that dictate the gel's consistency (e.g. hardness or rigidity) and contributes to its rheological properties (e.g. viscosity). Non-limiting examples of gel forming compounds include hydrogels, organogels, xerogels, and any combinations thereof.

In some embodiments, said at least one gel forming compound is selected from: (i) a biopolymer source such as for example: Gelatin, Alginate, Chitosan, Dextran, Collagen, Hyaluronic-acid, Polyglutamic-acid, and Elastin; (ii) semi-synthetic or synthetic polymer source, such as for example: Calcium polycarbophil, Acrylamides, Styrene maleic anhydride, Polyethylene oxide, Polyacrylic-acid, Polyethylene glycol, Carboxy Methyl Cellulose, Poly Vinyl Pyrrolidone, Sodium Polyacrylate, Hydroxypropyl Methyl Cellulose, and any combinations thereof. In further embodiments, said at least one gel forming compound is a combination of at least one compound from the list of group-i and at least one compound from the list of group-ii.

In some embodiments at least one gel forming compound of a composition of the invention may be further cross-linked.

In some other embodiments, said at least one gel forming compound has a swelling ratio of about 10 to 100 times-fold (w/w) (under conditions of: gastric pH at 37° C. for 1 hour).

The term "swelling ratio" represents the expansion extent of said gel forming compound between the state prior to adsorbing liquid (i.e. dry or semi dry form) and after adsorbing the maximal possible amount of liquid. Said swelling ratio is defined by weight-based and calculated according to the following equation: [wet weight−(dry weight*k)]/[(dry weight*k)]. The constant k represents the forming materials that are left after expansion of the device under the above conditions.

Gel forming compounds have the following advantages: (1) a much faster swelling degree that would be more useful for stomach specific delivery systems (2) unchanged molecular entity of the materials thus no alteration regarding the complex toxicity is expected. Gel forming compounds further provide rigid consistency to the compartment after absorption of liquid (refers herein to water or gastric fluid) that prevents to some degree leakage of the filler under bursting, rupturing and/or puncturing of the envelop-film. Moreover, gel forming compounds which are cross-linked reach higher rigidity than non-cross linked compounds.

In some embodiments said composition comprises at least one charged gel forming compound and at least one compound having an opposite charge, constructing a PEC (Poly Electrolyte Complex) formation upon liquid adsorption. In some embodiments, said at least one charged forming compound is selected from the following list: Polyvinyl acetate diethyl amino acetate (AEA), Poly-lysine, Chitosan, Polymethacrylate (Eudragit E), Poly-arginine. In other embodiments, said opposite charged compound is selected from the following list: Gelatin, Hyaluronic-acid, Sodium Poly-acrylate, Heparin, Poly acrylic-acid (Carbomer), Alginate, Pectin, Carboxy methyl cellulose. In some embodiments, at least one of said charged forming compound and/or at least one of said opposite charged compound, within said PEC, might be a gel forming compound and can be used for said device purposes.

In further embodiments, said at least one compound having an opposite charge, is added in excess (i.e. above the analytical amount of said charged gel forming compound). It is stipulated that addition of said at least one compound having an opposite charge in excess results in a large osmotic swelling force in addition to charge repulsion effect which together support in a massive fluid intake.

In some embodiments the ratio between said at least one charged gel forming compound and said at least one compound having an opposite charge is between about 99:1 to about 50:50. In other embodiments said ratio is about 99:1, 95:5, 90:10, 85:15, 80:20, 75:25, 70:30, 65:35, 60:40, 55:45, 50:50.

In some further embodiments said at least one charged gel forming compound is at least one SAP (Super Absorbent Polymer) allowing the swelling.

The term "Super Absorbent Polymer" is meant to encompass a number of cross-linked polymers, all have the basic ability to absorb massive quantities of liquids, such as water (or liquids containing water). They absorb water using the process of osmosis (water molecules pass through a barrier from one side to the other). When water passes the barrier (herein the external biodegradable film) and comes in contact with the polymer, the polymer swells. Non limiting examples of SAP are: Poly ethylene glycol (PEG), Poly glutamic-acid (PGA), Poly-acrylamide, Alginic-acid, Dextran, Poly acrylic-acid, Ethylene maleic, Carboxymethylcellulose (CMC), Pullulan, Starch, and any combinations thereof.

In yet further embodiments, said composition comprises at least one said charged forming compound acting as a linker within the PEC that forms a rigid gel within said at least one compartment that is non-leachable (i.e. the gel does not leach out of said compartment even upon break of said external biodegradable film).

Is some embodiments, said composition comprising said gel forming compound of said at least one compartment is being gradually degraded and disintegrated after it absorbs liquid and forms said gel. It is noted that degradation of said gel could be achieved by any process including: mechanical degradation (such as gastric/intestine pulses), chemical degradation (such as acidic/basic pH) or biological degradation (such as enzymatic activity).

In some further embodiments degradation of said at least one compartment is achieved after residing in the stomach for a period of between about 0.5 hrs to 30 days.

In some embodiments upon formation of a gel in said at least one compartment, said compartment reaches between about 50 to 90% of its full spreading at a period of between about 5-60 min after contact with stomach fluids. In other embodiments, said compartment reaches between about 50 to 90% of its full spreading at between about 10-20 min after contact with stomach fluids. In further embodiments, said compartment reaches between about 50 to 90% of its full spreading at between about 5-15 min after contact with stomach fluids.

In some embodiments upon formation of a gel in said at least one compartment, said compartment reaches at least about 50 to 90% of its maximal weight at between 5-120 min. In other embodiments, said compartment reaches at least 50 to 90% of its maximal weight at between about 10-60 min after contact with stomach fluids. In further embodiments, said compartment reaches at least 50 to 90% of its maximal weight at between about 15-30 min after contact with stomach fluids.

In some embodiments upon formation of a gel in said at least one compartment, said compartment reaches a rigidity that measured by holding maximal internal pressure of 0.15-1.50 atm. In other embodiments, said compartment readies rigidity under pressure of 0.50-1.00 atm. In further embodiments, said compartment reaches rigidity under pressure of 0.20-0.50 atm.

In some embodiments, the formation of a gel from said at least one gel forming compound in said at least one compartment may occur at pH ≤6. In other embodiments the formation of a gel from said at least one gel forming compound in said at least one compartment may occur at a pH of about 2, 3, 4, 5 or 6.

In other embodiments, the formation of a gel from said gel forming compound in said at least one compartment occurs under surrounding (i.e. liquid surrounding said compartment) conductivity of between about 5 to about 35 mS. In other embodiments the formation of a gel may occur at conductivity of about: 5, 10, 15, 20, 25, 30, 35 mS.

In some embodiments, at least one said gel forming compound is in the form of a powder. In other embodiments, at least one said gel forming compound is in the form of a liquid.

In some embodiments, at least one said gel forming compound is in the form of a film (referred as "gel-film" in some embodiments). Under these embodiments, said gel-film comprises film forming compounds (other than said gel forming compound listed above), such as for example: hydrophilic film-former, hydrophobic film former, non-degradable film former, degradable film former, plasticizers, binders, super absorbent polymers, co-polymers, osmognates, and so forth. Said gel-film may be formed by any method known in the art, including but not limited to: blowing, casting, extrusion, coating, lamination and any combination thereof.

In some embodiments, said gel-film comprises at least two layers. In further embodiments, at least one layer of said gel-film is composed of at least one gel forming compound. In other embodiments, said gel-film may be formed from at least two layers, each of which comprises independently at least one gel forming compound, which may be the same or different. In further embodiments, a device of the invention may comprise at least two (the same or different) gel films.

In some embodiments, said gel-film has a thickness of less than 1500 microns. In further embodiments, said gel-film has a thickness of between about 50 to about 300 microns. In yet other embodiments, said gel-film has a thickness of about 50, 60, 70, 80, 90, 100, 110, 120, 130, 140, 150, 160, 170, 180, 190, 200, 210, 220, 230, 240, 250, 300, 400, 500, 600, 700, 800, 900, 1000, 1100, 1200, 1300, 1400, 1500 microns. In further embodiments, said gel-film has a thickness of between about 160 to about 250 microns. In yet other embodiments, said gel-film has a thickness of about 160, 170, 180, 190, 200, 210, 220, 230, 240, 250 microns.

In some embodiments, said compartment may further comprise at least one gas forming compound. In other embodiments, at least one said gas and gel forming compounds are formulated into a single film (or a film having a single layer) (in some embodiments said film is a single layer film. In other embodiments said film is a multi layered film, i.e. at least two layers).

The term "gas forming compound" is meant to encompass any compound that is capable of absorbing any type of liquid(s) in contact therewith, thereby producing gas. In some embodiments the produced gas swells the compartment to form a three dimensional structure.

Non-limiting examples of gas forming compound are Sodium Carbonate, Sodium Bicarbonate, Ascorbic Acid, Fumaric Acid, Glutamic Acid, Sodium Acid Pyrophosphate, Citric Acid, Malic Acid, Tartaric Acid, Calcium Carbonate, Potassium Bicarbonate, and any combinations thereof.

In some embodiments, said external biodegradable film comprises at least one of a binder, plasticizer, pore-former, emulsifier, film-former, and any combinations thereof.

In some embodiments, said gel film comprises at least one additive selected from of a binder, plasticizer, gel-former, solvent, osmognate, and any combinations thereof.

Non limiting examples of a suitable hydrophilic film-former additives include: Polyvinylpyrrolidone (Plasdone, Kollidon), Polyvinyl alcohol, Kollicoat IR, Hydroxypropyl cellulose (Klucel), Methylcellulose, and any combinations thereof.

Non limiting examples of a suitable plasticizer include: Glycerin, Triethyl citrate (TEC), Triacetine (TRI), Tributyl citrate (TBC), Acetyl tributyl citrate (ATBC), Acetyl triethyl citrate, Polyethylene glycol (PEG 400-6000), Oleic acid, Castor oil, Diethyl phthalate (DEP), Propylene glycol, Dibutyl sebacate (DBS), Acetylated fatty-acid glycerides (Myvacet), Glycerol Mono Stearate (GMS), and any combinations thereof.

Non limiting examples of a suitable emulsifier include: Polysorbate, Triton X-100, Span, Glycerin, Glycerol Mono Stearate (GMS), and any combination thereof.

Non limiting examples of a suitable osmognate include: Sucrose, Dextrose, lactose, Fructose, NaCl, KCl, and any combinations thereof.

Non limiting examples of compounds suitable for forming said external biodegradable film include: Hypromellose Phthalate, Cellulose-Acetate-Phthalate, Hypromellose Acetate Succinate, Cellulose-Acetate, Ethyl-Cellulose, Poly-Methyl-Metacrylate, Poly-Ethyl-Acrylate, Poly-Vinyl-Acrylate-Phathalate, Poly-Vinyl-Acetate, Shellac, Carboxymethyl ethylcellulose (CMEC), and any combinations thereof.

Non limiting examples of a suitable solvent include: Ethanol, Methanol, Isopropanol, Acetone, Chloroform, Ethyl Acetate, and any combinations thereof.

In some embodiments, said gel forming film is part of at least one expandable multilayered biodegradable film comprising: at least one layer of external biodegradable film, and at least one expandable layer of at least one compound that capable to increase the volume of said film upon contact with liquid to an expanded volume forming at least one expandable compartment.

In some other embodiments, at least one layer of said multilayered film is enterically degradable (i.e. when said film is exposed to natural pH (in biological system or similar in vino environment, i.e. in the intestine) at least one of its properties deteriorates by reduction in one or more of tensile strength and/or elasticity).

The term "a gastric degradable swallowable capsule" is meant to encompass an external capsule encasing said at least one compartment being made of gastric degradable material and having a swallowable size (i.e. may be swallowed by a patient in need thereof). In some embodiments, said gastric degradable swallowable capsule has a size of about elongated 000 or 000 or 00 capsule or less (i.e. outer diameter of about 9.97 mm or less, height or locked length of about 30.0 mm or less and actual volume of about 1.68 ml or less). Table 1 below provides non-limiting capsule sizes suitable for the invention.

TABLE 1

Non-limiting capsule sizes

| Capsule size | Outer Diameter (mm) | Height or Locked Length (mm) | Actual Volume (ml) |
|---|---|---|---|
| Elongated 000 | 9.97 | 30.0 | 1.68 |
| 000 | 9.97 | 26.14 | 1.37 |
| 00 | 8.53 | 23.30 | 0.95 |
| 0 | 7.65 | 21.70 | 0.68 |
| 1 | 6.91 | 19.40 | 0.50 |
| 2 | 6.35 | 18.00 | 0.37 |
| 3 | 5.82 | 15.90 | 0.30 |
| 4 | 5.31 | 14.30 | 0.21 |
| 5 | 4.91 | 11.10 | 0.13 |

Non-limiting examples of gastric degradable capsules include the following manufacturers: Capsugel, Qualicap, ACG, Embo, Orpac, Chemcaps, Embocaps, Eei capsules and Golden capsules.

Non-limiting examples of gastric degradable capsules include the following: capsules made out of gelatin, capsule made out of non gelatin based compound (some type of such capsules are known as "Veggi" capsules).

Said capsule is capable of encasing within its volume void, said at least one compartment of a device of the invention so as to completely enclose said at least one compartment within said closed capsule. Uncasing said at least one compartment into said capsule may be performed by any method known in the art including: folding, rolling, creasing, collapsing, squeezing, pressing, wringing, cutting and so forth. Upon encasing said at least one compartment into said capsule, said compartment is defined to be in its closed or compressed form.

In some embodiments, a device of the invention comprises at least two compartments, each independently having an external biodegradable film, each independently enclosing composition, each has a 3D-shape when expanded in-situ.

In other embodiments, a device of the invention is encased within gastric degradable swallowable capsule at size of about elongated 000 or less. In other embodiments, a device of the invention comprises between 1 to 20 such said compartments.

In further embodiments, some of said compartments are connected in different lengths by using the compartment's excess of said external biodegradable film or/and by using an additional external joints such as any medical suture, including absorbable sutures, known in the art (for ex., Vicryl Rapide™ produced by ETHICON, or Dexon™ produced by COVIDIEN).

In yet further embodiments, at least two said expanded compartments form a 3-dimensional structure, or multi-structure construction containing repeatable (the same) or unrepeatable (different) of said structures. Structures type may be selected from the following non-limiting list including: ring, rod, octet, triangle, square, pentagon, hexagon or any other polygonal 3-dimensional shape.

In some embodiments, the distance between two said connected compartments herein joints lengths, is between about 0 to 15 mm. In other embodiments, this distance is about 0, 1, 2, 3, 4, 5, 6, 7, 8, 9, 10, 11, 12, 13, 14, 15 mm. In further embodiments, the distance between two said adjacent connected compartments is between about 0 to 7 mm. In yet further embodiments, the distance between two said adjacent connected compartments is between about 8 to 15 mm.

In some embodiments, the distance between two said connected structures herein joints lengths, is between about 0 to 30 mm. In other further embodiments, this distance is about 0, 1, 2, 3, 4, 5, 6, 7, 8, 9, 10, 11, 12, 13, 14, 15, 20, 25, 30 mm. In further embodiments, the distance between two said connected structures is between about 0 to 10 mm. In yet further embodiments, the distance between two said adjacent connected structures is between about 5 to 20 mm.

In some embodiments, the area of said compartments (at the open form, before folding and expansion) of a device of the invention is between about 25 to 60 $cm^2$. In other embodiments, this area is about 25, 30, 35, 40, 45, 50, 55, 60 $cm^2$. In further embodiments, this area is between about 1 to 35 $cm^2$. In yet further embodiments, this area is between about 55 to 100 $cm^2$. Said compartment's area is capable of encasing within said swallowable capsule.

In a further aspect of the invention there is provided a film comprising a composition comprising at least one super absorbent polymer (SAP) wherein said SAP is at least 60% of total weight of film.

In some embodiments of a film of the invention, said film comprises a composition comprising at least one super absorbent polymer (SAP) wherein said SAP is 60%, 65%, 70%, 75%, 80%, 85%, 90%, 95% of total weight of film.

In some embodiments said film has a thickness of 5 micron-500 micron.

In a further one of its aspects the invention provides a film comprising a composition comprising at least one gel forming compound and at least one binder compound and at least one continuous polymer layer; wherein said at least one gel forming compound is at least 60% of total weight of film. In some embodiments said film has a thickness of between about 5 microns-500 microns.

In yet a further aspect the invention provides a film comprising a composition comprising at least one gel forming compound and at least one binder compound and at least one continuous polymer layer; wherein said film having a thickness of between about 5 microns-500 microns.

In some embodiments a composition comprised in a film of the invention further comprises at least one PEC former. Upon absorption of liquid, said film of the invention forms a PEC-based rigid-gel having a three dimensional rigid shape that maintains its rigidity and shape for at least 0.5 hrs within said compartment after expansion. In some embodiments, said PEC-based rigid-gel having a three dimensional rigid shape maintains its rigidity and shape for at least 0.5, 1, 2, 3, 4, 5, 6, 7, 8, 12, 16, 24 hrs within said compartment after expansion.

In some embodiments, a film of the invention is used in a medical device for human care purposes, such as: baby diapers, adult protective underwear, sanitary napkins, wound dressing, hygienic pads, etc.

In a further aspect, the invention provides a device comprising at least one compartment having an external biodegradable film enclosing a composition comprising at least one gel forming compound;

wherein said at least one compartment is encased within a gastric degradable swallowable capsule; and wherein said at least one compartment is expanded in the stomach assuming a predefine structure that can be maintained in an expanded form for a predetermined time in the stomach.

Without being bound by theory, it is stipulated that a device of the invention is able to stimulate the mechanoreceptors on the stomach's wall thereby simulating a feeling of stomach fullness (as felt after eating a typical meal) by the treated patient and thus suppressing patient appetite for a predetermined period of time.

It is further stipulated that the simulation of a feeling of stomach fullness (thereby also may prolonging the intervals between meals-time periods) is achieved by use of a device of the invention so that it induces stomach detention and slows stomach emptying period.

In another aspect, the invention provides a device as defined herein above and below, for use in inducing weight loss in a patient.

The term "inducing weight loss in a patient" should be understood to encompass any qualitative or quantitative loss of body weight in a subject administered with a device of the invention.

In a further aspect, the invention provides a device as defined herein above and below, for use in curbing appetite in a patient.

The term "curbing appetite in a patient" should be understood to encompass any qualitative or quantitative loss of appetite (i.e. any qualitative or quantitative reduction in the caloric intake of a subject or any qualitative or quantitative reduction in patient craving for food) in a subject administered with a device of the invention.

In another aspect of the invention, a device as defined herein above and below is used in promoting satiety and/or satiation.

The term "promoting satiety and/or satiation" is meant to encompass any qualitative or quantitative promotion of feeling of satiety and/or of satiation (i.e. feeling of stomach fullness or lesser urge for food) by a patient administered with a device of the invention, immediately upon food consumption, after food consumption or in between feedings.

In a further aspect, the invention provides a method of inducing weight loss in a patient comprising administering a device as defined herein above and below to said patient.

In a further aspect, the invention provides a method for promoting satiety and/or satiation in a patient comprising administering a device as defined herein above and below to said patient.

In yet a further aspect, the invention provides a method of curbing appetite in a patient comprising administering a device as defined herein above and below to said patient.

In all methods of the invention, said device may be administered concomitantly, sequentially or simultaneously with any other treatment method for either curbing appetite, promoting satiety, and/or weight loss in a patient (including but not limited to administration of additional active agent, participation in an exercise and/or diet program of said patient and participation in a psychological treatment of said patient).

In another one of its aspects, the invention provides a kit comprising a device as defined herein above and below and instructions for use thereof.

In some embodiments, said kit of the invention further comprises means for delivering the device into a stomach of a patient.

In other embodiments, said kit of the invention further comprises a degradation formulation which when contacted with said device in a stomach of a patient, structurally degrades the device and/or accelerates the degradation of the device.

BRIEF DESCRIPTION OF THE DRAWINGS

In order to understand the disclosure and to see how it may be carried out in practice, embodiments will now be described, by way of non-limiting example only, with reference to the accompanying drawings, in which.

DETAILED DESCRIPTION OF EMBODIMENTS

1. General Structure of a Device of the Invention

While looking for in-situ expanding & degradable intragastric device it has been founded that a device containing high swelling-ratio agent wrapped with an ultrathin film is capable of bursting out of a 000 or 00-(gelatin or vegetarian) capsule and swells into a stiff tri-dimension shape with an effective volume inside the gastric. Said internal solid-like gel/gas construction (herein the swelling-ratio agent) enables the whole device of the invention to be maintained in the stomach and not be evacuated too easily into the intestine. In order to facilitate insertion of such swelling agent compound into the volume of a standard 000/00-capsule (designed for oral administration), some embodiments of the invention provide a thin film as the envelope-layer forming a compartment that holds tire swelling agent in a form of a film. The integration of both swelling agent film and envelope-film enables the compact encapsulation within the swallowable capsule.

In some embodiments, a device is composed of 3 major elements: (i) an outer gelatin or vegetarian capsule at 000/00-size (commercially purchased) which used as the device's shell; (ii) a thin synthetic polymers-based microfilm which used as the envelope-layer of the swelling filler; and (iii) a polymers-based hydrogel-film and/or gel-gas forming film which used as the swelling filler.

2. Composition of an External Biodegradable Envelope-Film of a Device of the Invention In some embodiments of the invention, an envelope-film is composed of at least two layers pre-casted upon a support sheet. The support sheet, in a form of film or substrate [Teflon® film, Teflon® coated substrate, silicon film, silicon made or coated substrate, PET (polyethylene terephthalate) film, BoPET film, Melinex®, MYLAR-A®, Hostaphan®, Kapton® (polyimide) film], enables the casting of a first-layer without an adhesive material. The first casted-layer (composed of one or combination of, but not limited to, PVOH or hydroxypropylcellulose or Kollicoat-IR® or methylcellulose or hypromellose or Povidone or polyvinylpyrrolidone) provides elasticity and protection for the other casted layers during manufacturing and storage of the final device since the support sheet is actually detached and removed in the course of the final device preparation. The other casted layers (composed of, but not limited to, HP-55: DEP:Ethocel-45:Klucel or EudragitL100-55:EudragitRS: TEC:GMS or CAP:DEP:CA: or AS-LF:CA:DEP:ATBC or Cellulose Acetate:PEG 400:TEC) provide the major structure of the envelope-film and are the only layers dial actually endures under the acidic solution of the stomach.

Non-limiting examples of envelope-film compounds include:
- Polyethylene-Phthalate polymer film; purchased as film (MYLAR-A®; DuPont, USA).
- Polyvinyl Alcohol 4-88; purchased as powder (Merck, Germany)—
- Methocel LV-50; purchased as powder (DOW, USA)
- Poly-Vinyl-Alcohol[PVA]:Poly-Ethylene-Glycol[PEG] graft-copolymer; purchased as powder (Kollicoat-IR®; BASF, Germany)
- Hydroxy-Propyl-Cellulose polymer; purchased as powder (Klucel-LF®; Ashland, USA) Povidone (Kollidone 25; BASF, Germany).
- Hypromellose Phthalate [HP-55] and Hypromellose Acetate Succinate [AQOAT AS-LF]; purchased as powders (Shin-Etsu, Korea) CAP [Cellulose-Acetate-Phthalate] and CA [Cellulose-Acetate]; purchased as powders (Eastman, USA).
- Triethyl citrate [TEC] and Acetyl tributyl citrate [ATBC]; purchased as liquids (Merck, Germany).
- DEP [Diethyl-Phthalate]; purchased as liquid (Spectrum, USA)—.
- Glycerol Monostearate [GMS]; purchased as liquid (Cognis, Germany)—.

Ethanol, Methanol, Isopropyl Alcohol [IPA], Ethyl Acetate, Acetic-acid, and Acetone (BioLab, Israel) are organic solvents used for the polymers dissolving.

3. Process for the Manufacture of the External Envelope Biodegradable Film of a Device of the Invention Example 1

The manufacture of an envelope-film is based on solutions preparation followed by two casting processes performed:
1) Polyvinyl alcohol Solution (PVOH)—PVOH powder is dissolved in Water.
2) PVOH Casting—The PVOH solution is casted as the first-layer upon the support sheet and kept to dry.
3) HP-55:DEP:Ethocel-45:Klucel (60:20:15:5; % ratio) Solution—Hypromellose phthalate (HP-55) powder and Ethocel-45 powder (in this order) are first dissolved in Acetone, followed by the addition of DEP solution. Then, pre-prepared Klucel solution is added.
4) HP-55:DEP:Ethocel-45:Klucel Casting—The HP-55: DEP:Ethocel-45:Klucel solution is casted as the second-layer upon the dry PVOH (first-layer) film and kept to dry.

Example 2

The manufacture of an envelope-film is based on solutions preparation followed by two casting processes performed:
1) Hydroxypropyl cellulose Solution—Klucel LF powder is dissolved in Ethanol
2) Klucel LP Casting—The Klucel LF solution is casted as the first-layer upon the support sheet and kept to dry
3) Eudragit L100-55:Eudragit RS:TEC:GMS (60:15:20: 5; % ratio) Solution—Eudragit L100-55 powder and Eudragit RS powder (in this order) are first dissolved in a mixture of Acetone:IPA (65:35), followed by the addition of TEC (purchased as a solution). Then, Glycerol Monostearate (GMS) solution is added.
4) Eudragit L100-55:Eudragit RS:TEC:GMS Casting—The Eudragit L100-55:Eudragit RS:TEC:GMS solution is casted as the second-layer upon the dry Klucel LF (first-layer) film and kept to dry Example 3

The manufacture of an envelope-film is based on solutions preparation followed by two casting processes performed:
1) Kollicoat Solution—Kollicoat-IR powder is dissolved in Ethanol:Water (1:1) solution.
2) Kollicoat Casting—The Kollicoat solution is casted as the first-layer upon the support sheet and kept to dry
3) CAP:DEP:CA (70:20:10% ratio) Solution—CAP powder and CA powder (in this order) are first dissolved in Acetone, followed by the addition of DEP solution. Then, pre-prepared Klucel solution is added.
4) CAP:DEP:CA: Casting—The CAP:DEP:CA: solution is casted as the second-layer upon the dry Kollicoat (first-layer) film and kept to dry Example 4

The manufacture of an envelope-film is based on solutions preparation followed by two casting processes performed:
1) Methyl cellulose Solution—Methocel EV-50 powder is dissolved in Water.
2) Methocel Casting—The Methocel EV-50 solution is casted as the first-layer upon the support sheet and kept to dry.
3) AS-LF:CA:DEP:ATBC (65:15:10:10; % ratio) Solution—Hypromellose Acetate Succinate (AS-LP) powder and Cellulose Acetate (CA) powder (in this order) are first dissolved in Acetone, followed by the addition of DEP solution and ATBC (purchased as solutions).
4) AS-LF:CA:DEP:ATBC Casting—The AS-LF:CA: DEP:ATBC solution is casted as the second-layer upon the dry Methocel (first-layer) film and kept to dry Example 5

The manufacture of an envelope-film is based on solutions preparation followed by two casting processes performed:
1) Plasdone Solution—Kollidon 25 powder is dissolved in Ethanol
2) Kollidon 25 Casting—The Kollidon 25 solution is casted as the first-layer upon the support sheet and kept to dry
3) Cellulose Acetate:PEG 400:TEC (75:10:15% ratio) Solution—Cellulose Acetate powder is first dissolved in Acetone, followed by the addition of PEG 400 solution.
4) Cellulose Acetate:PEG 400 Casting—The Cellulose Acetate:PEG 400 solution is casted as the second-layer upon the dry Kollidon 25 (first-layer) film and kept to dry.

4. Composition of a Hydrogel-Film of a Device of the Invention

In some embodiments of the invention the hydrogel-film is composed of at least two layers pre-casted upon a support sheet (described above). The support sheet enables the casting of the first-layer (PVOH or Klucel or Kollicoat-IR® or Methocel or Povidone) without an adhesive material, while it provides elasticity and protection for the other casted layers during manufacturing and storage of the final device since the support sheet is actually detached and removed in the course of the device preparation. However, the casted layers [Luquasorb(FP800):Lactose:PEG:Kollidon or Carbopol:Chitosan:PEG:Klucel or Poly-Acrylic-Acid: Chitosan:PEG:Klucel or SephadexG-100:Lactose:TEC: Klucel] contain: particles suspension (rather than a polymer solution) of polymers that compose a swellable gel-matrix, plasticizer and binder to assemble the particles into a suspension.

Non-limiting list of hydrogel compounds include:

Polyethylene-Phthalate polymer; purchased as film (MYLAR-A®; DuPont, USA).

Polyvinyl alcohol polyethylene glycol graft copolymer; purchased as powder (Kollicoat-IR®; BASF, Germany).

Povidone (Kollidone 25; BASF, Germany).

Polyvinyl Alcohol 4-88; purchased as powder (Merck, Germany)—.

Methocel LV-50; purchased as powder (DOW, USA).

Poly-Vinyl-Alcohol[PVA]:Poly-Ethylene-Glycol[PEG] graft-copolymer; purchased as powder (Kollicoat-IR®; BASF, Germany).

Hydroxy-Propyl-Cellulose polymer; purchased as powder (Klucel-LF®; Ashland, USA).

Cross-linked Sodium Polyacrylic-Acid; purchased as powder (Luquasorb®; BASF, USA)—.

Cross-linked Poly Glutamic-Acid; purchased as powder (PGA; hayashibira, Japan).

Cross-linked Poly-Acrylic-Acid; purchased as powder (Carbopol 974; Lubrizol, USA).

Cross-linked Sodium Polyacrylic-Acid; purchased as powder (FavorPac®; Evonik, Germany).

Cross-linked Dextrane gel; purchased as powder (Sephadex G-100; GE Medical).

Chitosan; purchased as powder (Chitoclear®; Pre mix, Iceland or 90/200/A1; Kraeber, Germany or Protasan UP CL 114, 113, 213, 214; Novamatrix, Norway).

Poly-Ethylene-Glycol; purchased as liquid (PBG-400; Sigma, USA)—.

Chitosan; purchased as powder (KiOnutrime-CsG; kitozyme, Belgium)—.

Lactose monohydrate; purchased as powder (Pharmatose 200, Fonterra, New Zealand).

5. Process for the Manufacture of a Hydrogel-Film of a Device of the Invention

Example 1

The manufacture of the hydrogel-film is generally similar to the manufacture of the envelope-film; slurries (in this case one solution and one suspension) preparation followed by two casting processes performed at RT:

1) Polyvinyl alcohol Solution—PVOH powder is dissolved in Water

2) PVOH Casting—The PVOH solution is casted as the first-layer upon the support sheet and kept to dry.

3) Sephadex G-100:Lactose:TEC:Klucel (70:10:5:15; % ratio) Suspension—Sephadex and Lactose monohydrate granules are first ground. The Sephadex particles are then added to a Klucel solution, and after mixing the Lactose particles are added and mixed, forming a particles suspension. Finely TEC is added into the suspension under mixing.

4) Sephadex:Lactose:TEC:Klucel Casting—The suspension is casted as the second-layer upon the dry PVOH (first-layer) film and kept to dry Example 2

The manufacture of the hydrogel-film is generally similar to the manufacture of the envelope-film; slurries (in this case one solution and one suspension) preparation followed by two casting processes performed at RT:

1) Polyvinyl alcohol Solution—PVOH powder is dissolved in Water

2) PVOH Casting—The PVOH solution is casted as the first-layer upon support sheet and kept to dry.

3) Luquasorb(FP800):Lactose:PEG:Kollidon (75:10:5: 10; % ratio) Suspension—Luquasorb and Lactose monohydrate granules are first ground. The Luquasorb particles are then added to a Kollidon solution, and after mixing, the lactose particles are added and mixed, forming a particles suspension. Finely, PEG is added into the suspension under mixing.

4) Luquasorb(FP800):Lactose:PEG:Kollidon Casting—The suspension is casted as the second-layer upon the dry Kollicoat (first-layer) film and kept to dry Example 3

The manufacture of the hydrogel-film is generally similar to the manufacture of the envelope-film; slurries (in this case one solution and one suspension) preparation followed by two casting processes performed at RT:

1) Kollicoat Solution—Kollicoat-IR powder is dissolved in Ethanol:Water (1:1) solution 2) Kollicoat Casting—The Kollicoat solution is casted as the first-layer upon the support sheet and kept to dry.

3) FavorPac(FP):Chitosan(CS):PEG:Klucel (65:15:10: 10; % ratio) Suspension—FP and CS granules are first ground. The FP particles are then added to a Klucel solution, and after mixing, the CS particles are added and mixed, forming a particles suspension. Finely, PEG solution is added into the suspension under mixing.

4) FavorPac:Chitosan:PEG:Klucel Casting—The suspension is casted as the second-layer upon the dry Kollicoat (first-layer) film and kept to dry Example 4

The manufacture of the hydrogel-film is generally similar to the manufacture of the envelope-film; slurries (in this case one solution and one suspension) preparation followed by two casting processes performed at RT:

1) Kollicoat Solution—Kollicoat-IR powder is dissolved in Ethanol:Water (1:1) solution 2) Kollicoat Casting—The Kollicoat solution is casted as the first-layer upon the support sheet and kept to dry 3) Carbopol 974 solution (1.5%) is dissolved in water and 1.75M NaOH solution is added under steering to raise pH 5-5.5 where stable gel is accepted. Then gel is dried in oven.

4) Carbopol:Chitosan(CS):PEG:Klucel (65:15:5:15; % ratio) Suspension—Carbopol and CS granules are first ground. The Carbopol particles are then added to a Klucel solution, and after mixing, the CS particles are added and mixed, forming a particles suspension. Finely, PEG solution is added into the suspension under mixing.

5) Carbopol:Chitosan:PEG:Klucel Casting—The suspension is casted as the second-layer upon the dry Kollicoat (first-layer) film and kept to dry.

6. Composition of a Gel-Gas Forming Film of a Device of the Invention

In some embodiments of the invention the gel-gas forming film is composed of at least two layers pre-casted upon a support sheet (described above). The support sheet enables the casting of the first-layer without an adhesive material, while it provides elasticity and protection for the other casted layers during manufacturing and storage of the final device since the support sheet is actually detached and removed in the course of the device preparation. However, the other casted layers contain particles suspension (rather than a polymer solution) of polymers that composes a gel producing-matrix, gas producing-matrix, plasticizer and binder to assemble the particles into a suspension.

Non-limiting list of gas-producing compounds include:
Polyethylene-Phthalate polymer film (MYLAR-A®; DuPont, USA) Polyvinyl alcohol polyethylene glycol graft copolymer (Kollicoat-IR®; BASF, Germany) Polyvinyl Alcohol 4-88; purchased as powder from Merck—the first casted layer—is used as the surface coater for the second layer.
Sodium Bicarbonate (Brunner Mond, UK)
Citric Acid (Merck, Germany) Malic Acid (Sigma, USA) Tartaric Acid (Sigma, USA)
Calcium Carbonate (Sigma, USA).
Poly-Ethylene-Glycol (PEG-400; Sigma, USA) Hydroxy-Propyl-Cellulose polymer (Klucel-LF®; Ashland, USA) and Polyvinylpyrrolidone (Kollidon 25, BASF, USA)

7. Process for the Manufacture of a Gel-Gas Forming Film of a Device of the Invention Example 1

The manufacture of gel-gas forming film is generally similar to the manufacture of the envelope-film or the Gel-film; slurries (in this case one solution and one suspension) preparation followed by two casting processes performed at RT:

1) Kollicoat Solution—Kollicoat-IR powder is dissolved in Ethanol:Water (1:1) solution
2) Kollicoat Casting—The Kollicoat solution is casted as a first-layer upon the support sheet and kept to dry
3) Sodium Bicarbonate (NaHCO3):Citric Acid (C6H8O7):PEG:Klucel (50:30:8:12; % ratio) Suspension. The C6H8O7 particles are then added to a Klucel solution (10% powder pre-dissolved in Ethanol), and after mixing, the NaHCO3 particles are added and mixed, forming a particles suspension. Finely PEG is added into the suspension under mixing.
4) Sodium Bicarbonate (NaHCO3):Citric Acid (C6H8O7):PEG:Klucel Casting—The suspension is casted as a second-layer upon the dry Kollicoat (first-layer) film and kept to dry Example 2

The manufacture of the gas forming film is generally similar to the manufacture of the envelope-film or the Gel-film; slurries (in this case one solution and one suspension) preparation followed by two casting processes performed at RT:

1) Kollicoat Solution—Kollicoat-IR powder is dissolved in Ethanol:Water (1:1) solution
2) Kollicoat Casting—The Kollicoat solution is casted as a first-layer upon the support sheet and kept to dry
3) Calcium Carbonate (CaCO3):Tartaric Acid (C4H6O6):PEG:Klucel (33.2:49.8:5:12; % ratio) Suspension.

The C4H6O6 particles are then added to a Klucel solution (10% powder pre-dissolved in Ethanol), and after mixing, the CaCO3 particles are added and mixed, forming a particles suspension. Finely PEG is added into the suspension under mixing.
4) Calcium Carbonate (CaCO3):Tartaric Acid (C4H6O6):PEG:Klucel Casting—The suspension is casted as a second-layer upon the dry Kollicoat (first-layer) film and kept to dry Example 3

The manufacture of the gas forming film is generally similar to the manufacture of the envelope-film or the Gel-film; slurries (in this case one solution and one suspension) preparation followed by two casting processes performed at RT:

1) PVOH Solution—PVOH powder is dissolved in Ethanol:Water (1:1) solution
2) PVOH Casting—The PVOH solution is casted as a first-layer upon the support sheet and kept to dry
3) Potassium Bicarbonate ($KHCO_3$):Tartaric Acid ($C_4H_6O_6$):PEG:Klucel (47.4:35.6:5:12; % ratio) Suspension.

The C4H6O6 particles are then added to a Klucel solution (10% powder pre-dissolved in Ethanol), and after mixing, the KHCO3 particles are added and mixed, forming a particles suspension. Finely PEG is added into the suspension under mixing.
4) Potassium Bicarbonate (KHCO3):Tartaric Acid (C4H6O6):PEG:Klucel Casting—The suspension is casted as a second-layer upon the dry PVOH (first-layer) film and kept to dry 8. Process for the Manufacture of a Device of the Invention 1) Forming an envelope film (for example as described above in Section 3, Examples 1-5);
2) Forming a gel film (for example as described above in Section 5, Examples 1-4) and/or gas-gel film (for example as described above in Section 7. Examples 1-3);
3) Creating a multi-layered formation of envelope and gel films (as an alternative, forming a multilayered biodegradable film comprising both features of said envelope layer and said expandable layer);
4) Cutting and connecting the multi layered formation to form a compartment and compartments structure;
5) Folding the compartment/s into a swallowable capsule.

9. Process for the Manufacture of a Device of the Invention

1) Forming an envelope film (for example as described above in Section 3, Examples 1-5);
2) Casting a gel film (for example as described above in Section 5, Examples 1-4) and/or gas-gel film (for example as described above in Section 7, Examples 1-3) on selected area;
3) Casting or attaching another envelope film (for example as described above in Section 3, Examples 1-5);
4) The above process creates a multi-layered formation of envelope and gel films (as an alternative, forming a multi-layered biodegradable film comprising both features of said envelope layer and said expandable layer);
5) Cutting and connecting the multi layered formation to form a compartment and compartments structure;
6) Folding the compartment/s into a swallowable capsule.

10. Shape and Form of a Device of the Invention

The present invention provides a device comprising at least one compartment having an external biodegradable film enclosing at least one gel forming compound or one gel/gas forming compound, wherein said at least one compartment is encased within a gastric degradable swallowable capsule.

Figure 2:
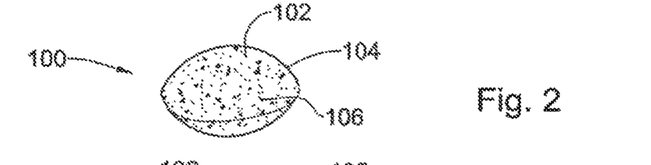
FIG. 2 is a schematic view of one compartment of an orally administrable device according to the invention, having a 3-dimensional "ellipse" shape at the expanded form, where the expanded-film is swelled after contact with gastric fluids.
Figure 3:
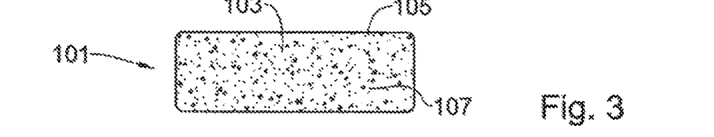
FIG. 3 is a schematic top-view of one compartment of an orally administrable device according to the invention, having a 3-dimensional "rectangle" shape at the expanded form where the expandable-film is swelled after contact with gastric fluids.

FIG. 2 and FIG. 3 present schematic illustrations of the expanded form of an orally administrable device of the invention (100 and 101 respectively) having one compartment (102 and 103 respectively) having an external biodegradable film (104 and 105 respectively), wherein said expansion of device occurs due to the contact of the expandable-film with gastric fluids forming a gel matrix within said compartment (106 and 107 respectively).

In some embodiments a device of the invention comprises at least two, three, four, five, six, seven, eight, nine, ten, eleven, twelve, thirteen, fourteen, fifteen, sixteen, seventeen, eighteen, nineteen, twenty individual compartments (that may be the same or different, in either contents or external biodegradable film), having each an external biodegradable film enclosing at least one gel forming compound or one gel/gas forming compound in each compartment, wherein said compartments are encased within a gastric degradable swallowable capsule.

Figure 4:
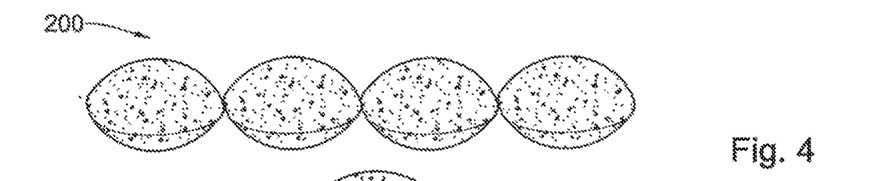
FIG. 4 is a schematic view of four connected compartments of an orally administrable device according to the invention, which form an "open chain" shape at the expanded form, where the expandable-film is swelled after contact with gastric fluids.
Figure 5:
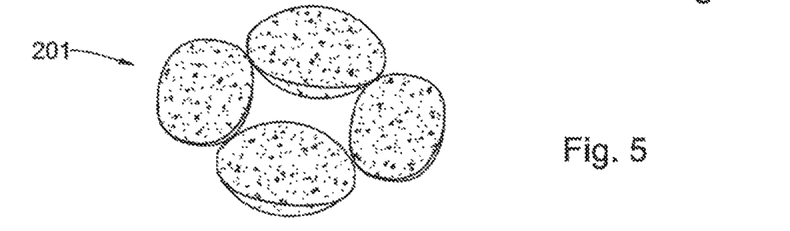
FIG. 5 is a schematic view of four connected compartments of an orally administrable device according to the invention, which form a "closed chain" shape at the expanded form, where the expandable-film is swelled after contact with gastric fluids.

In some embodiments, said device comprises four compartments: FIG. 4 presents a schematic view of orally administrable device according to the invention (200), which comprises four compartments forming an "open chain shape" at the expanded form; FIG. 5 presents a schematic view of orally administrable device according to the invention (201), which comprises four compartments forming a "closed chain shape" at the expanded form.

Figure 6:
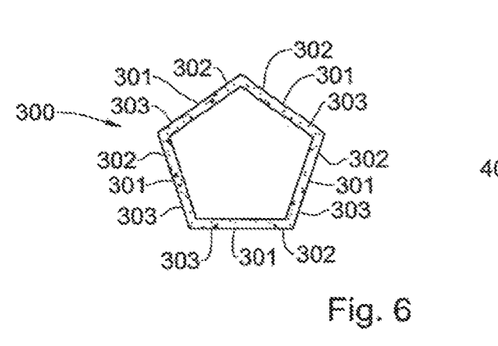
FIG. 6 is a schematic lop-view of five connected compartments of an orally administrable device according to the invention, which form a "pentagon" shape" at the non-expanded form (where the expandable-film is not swelled) before folding into swallowable capsule.

In some embodiments, said device comprises five compartments; FIG. 6 presents a schematic view of an orally administrable device according to the invention (300), having five compartments (301) forming a "closed chain shape" (in the form of a pentagon) at its non-expanded form before folding into swallowable capsule, each having an external biodegradable film (302) and a composition capable of expanding said compartment upon absorption of liquids (303).

Figure 7:
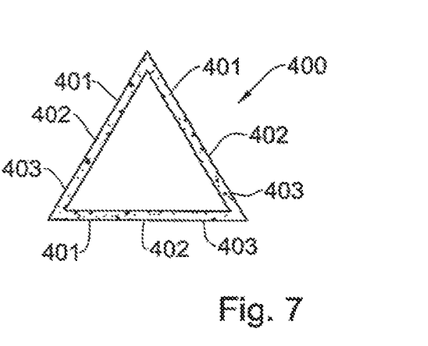
FIG. 7 is a schematic top-view of three connected compartments of an orally administrable device according to the invention, which form a "triangle shape" at the non-expanded form (where the expandable-film is not swelled) before folding into swallowable capsule.

In some embodiments, said device comprises three compartments: FIG. 7 presents a schematic view of an orally administrable device according to the invention (400), having three compartments (401) forming a "closed chain shape" (in the form of a triangle) at its non-expanded form before folding into swallowable capsule, each having an external biodegradable film (402) and a composition capable of expanding said compartment upon absorption of liquids (403).

In some embodiments, said device comprises up to twenty connected compartments lightly encasing within a small volume.

Figure 8:
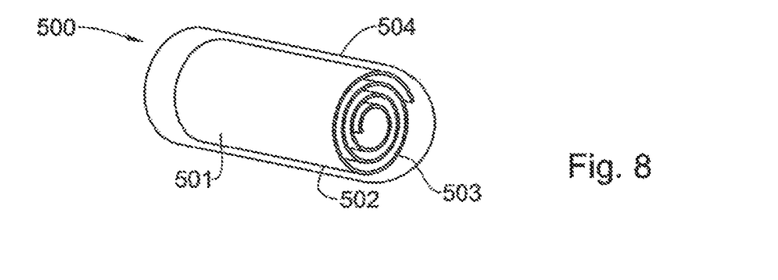
FIG. 8 and FIG. 10 are schematic views of one or several connected compartments of an orally administrable device according to the invention, at the non-expanded form (where the expandable-film is not swelled), rolled (in FIG. 8) or folded (in FIG. 10) and encased within a swallowable capsule before use.

FIG. 8 presents a schematic view of a device of the invention (500) having several connected compartments at the non-expanded form rolled (501) having an external biodegradable film (502), said three compartments comprise a composition capable of expanding the compartment upon exposure to liquid (503). Said compartment is encased within a swallow-able capsule (504).

Figure 10:
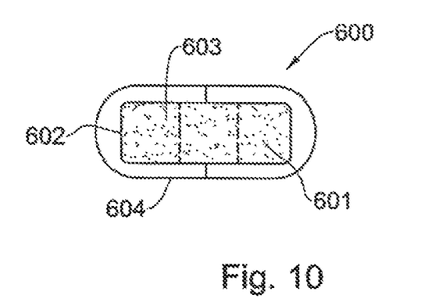

FIG. 10 presents a schematic view of an orally administrable device according to the invention (600), having three connected compartments at the non-expanded form folded (601), having an external biodegradable film (602), said three compartments comprise a composition capable of expanding the compartment upon exposure to liquid (603) and encased within a swallowable capsule (604).

Figure 9:
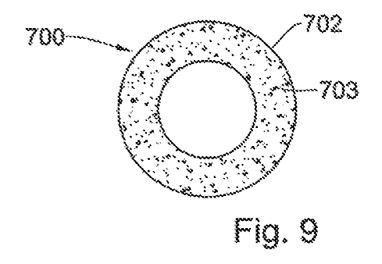
FIG. 9 is a schematic top-view of one compartment or several connected compartments of an orally administrable device according to the invention, which forms a "ring shape" at the expanded form, where the expandable-film is swelled after contact with gastric fluids.

In some embodiments, said at least one compartment will have any shape including but not limited to rectangular, ring (round), polygon, and so forth: FIG. 9 presents a schematic view of at least one compartment (700) of an orally administrable device according to the invention, which forms a "ring shape" at the expanded form, where the expandable-film is swelled after contact with gastric fluids. Said compartment having an external biodegradable film (702), and a composition expanding the compartment upon exposure to liquid (703).

Figure 11:
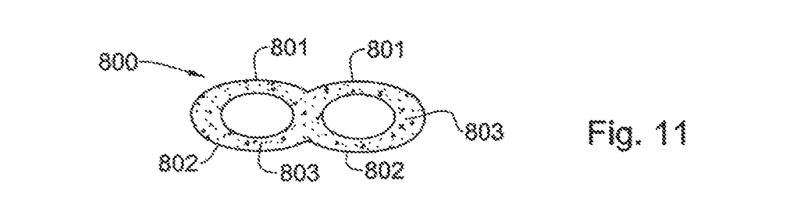
FIG. 11 is a schematic lop-view of one compartment or several connected compartments of an orally administrable device according to the invention, forming an "octet" structure at the expanded form, where the expandable-film is swelled after contact with gastric fluids.

FIG. 11 presents a schematic view of at least one compartment (800) or an orally administrable device according to the invention, formed of two interconnected rings (801) having a mutual overlapping volume or being connected only at the outer external envelope, at the expanded form, where the compartment is expanded after contact with gastric fluids. Said compartment having an external biodegradable film (802), and a composition expanding the compartment upon exposure to liquid (803).

Figure 12:
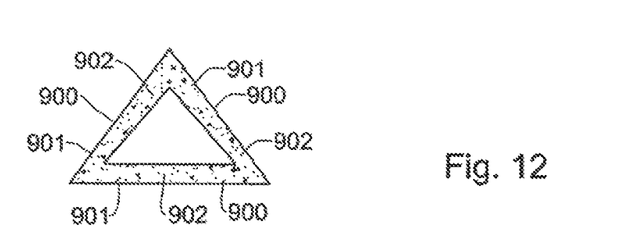
FIG. 12 is a schematic top-view of three connected compartments of an orally administrable device according to the invention, which form a "triangle shape" at the expanded form, where the expandable-film is swelled after contact with gastric fluids.

FIG. 12 presents a schematic view of three compartments (900) of an orally administrable device according to the invention, which form a "triangle shape" at the expanded form where the compartment is swelled after contact with gastric fluids. Said compartment having an external biodegradable film (902), and a composition expanding the compartment upon exposure to liquid (903).

Figure 13:
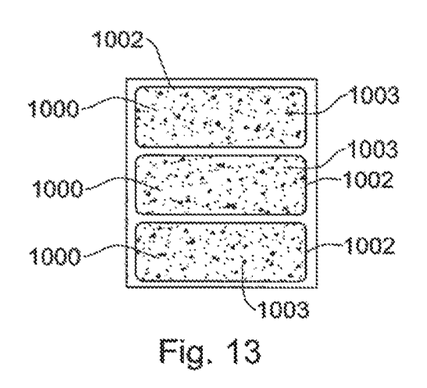
FIG. 13 is a schematic view of three connected compartments of an orally administrable device according to the invention, which form a "square shape" at the non-expanded form (where the expand able-film is not swelled) before folding into swallowable capsule.

FIG. 13 is a schematic view of four compartments (1000) of an orally administrable device according to the invention, which form a "square shape" at the non-expanded form (where the expandable-film is not swelled) before folding into swallowable capsule. Said compartments having an external biodegradable film (1002), and a composition expanding the compartment upon exposure to liquid (1003).

Figure 14:
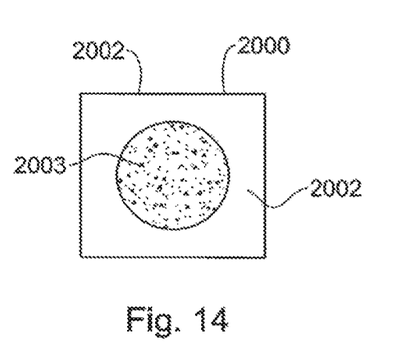
FIG. 14 is a schematic top-view of one compartment of an orally administrable device according to the invention, which forms a "square shape" at the non-expanded form (where the expandable-film is not swelled) before folding into swallowable capsule, and "ball" structure at the expanded form where the expandable-film is swelled alter contact with gastric fluids.

FIG. 14 is a schematic view of one compartment (2000) of an orally administrable device according to the invention, which forms a "square shape" at the expanded form where the expandable-film is swelled after contact with gastric fluids. Said compartments having an external biodegradable film (2002), and a composition expanding the compartment upon exposure to liquid (2003).

Figure 15:
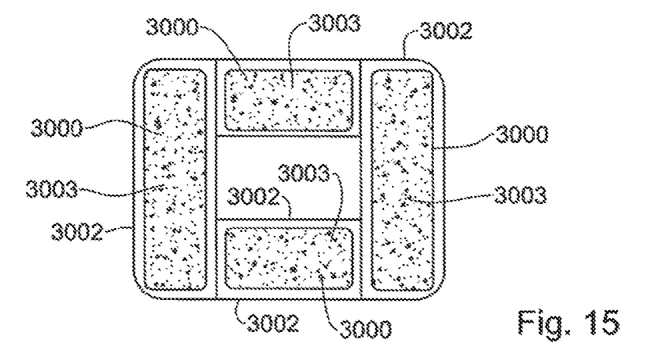
FIG. 15 is a schematic top-view of four connected compartments of an orally administrable device according to the invention, which form a "square shape" at the non-expanded form (where the expandable-film is not swelled) before folding into swallowable capsule.

FIG. 15 is a schematic view of four compartments (3000) of an orally administrable device according to the invention, which form a "square shape" at the non-expanded form (where the expandable-film is not swelled) before folding into swallowable capsule. Said compartments having an external biodegradable film (3002), and a composition expanding the compartment upon exposure to liquid (3003).

Figure 16:
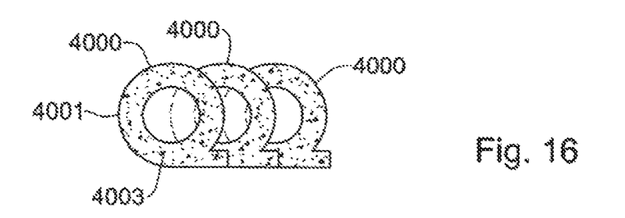
FIG. 16 is a schematic view of three connected compartments of an orally administrable device according to the invention, which form a "multi-rings shape" at the expanded form, where the expandable-film is swelled after contact with gastric fluids.

In some embodiments, said device composed of a multi-structure shape; FIG. 16 is a schematic view of three rings (4000) of an orally administrable device according to the invention, connected together to form a tri-dimensional shape at the expanded form where the expandable-film is swelled after contact with gastric fluids. Said compartments having an external biodegradable film (4001), and a composition expanding the compartment upon exposure to liquid (4003).

Figure 17:
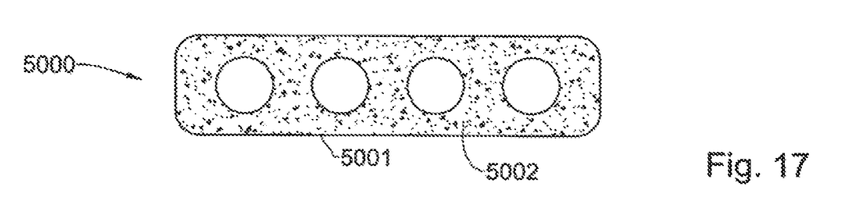
FIG. 17 is a schematic view of one compartment or several connected compartments of an orally administrable device according to the invention, forming a "submarine shape" at the expanded form, where the expandable-film is swelled after contact with gastric fluids.

FIG. 17 is a schematic view of one compartment or several connected compartments of an orally administrable device according to the invention (5000), forming a "submarine shape" at the expanded form where the expandable-film is swelled after contact with gastric fluids. Said compartments having an external biodegradable film (5001), and a composition expanding the compartment upon exposure to liquid (5002).

Figure 18:
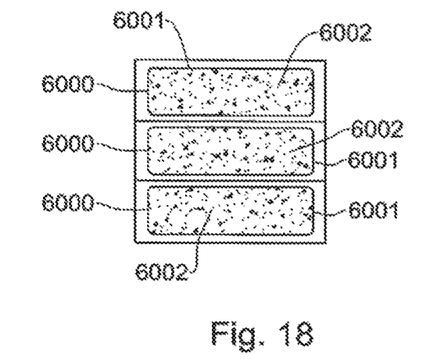
FIG. 18 is a schematic top-view of three connected compartments of an orally administrable device according to the invention, which form a "square shape" at the non-expanded form (where the expandable-film is not swelled top view) before folding into swallowable capsule, and a "sea mattress" at the expanded form where the expandable-film is swelled after contact with gastric fluids.

FIG. 18 presents a schematic view of three compartments (6000) of an orally administrable device according to the invention, which form a "square shape" at the non-expanded form (where the compartment is not swelled) before folding into swallowable capsule, and a "sea mattress" structure at the expanded form where the hydrogel-film is swelled after contact with gastric fluids. Said compartments having an external biodegradable film (6001), and a composition expanding the compartment upon exposure to liquid (6002).

Figure 19:
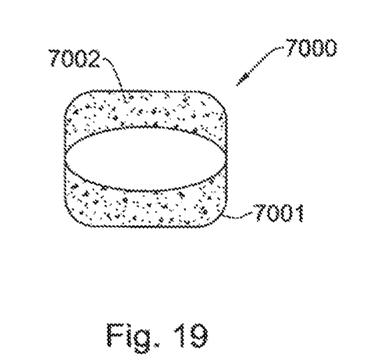
FIG. 19 is a schematic view of one compartment or several connected compartments of an orally administrable device according to the invention, forming a "square shape" with an elliptic hollow inside at the expanded form, where the expandable-film is swelled after contact with gastric fluids.

FIG. 19 is a schematic view of three compartment is (7000) of an orally administrable device according to the invention, which form a "square shape" with an elliptic hollow inside at the expanded form where the expandable-film is swelled after contact with gastric fluids. Said compartments having an external biodegradable film (7001), and a composition expanding the compartment upon exposure to liquid (7002).

Figure 20:
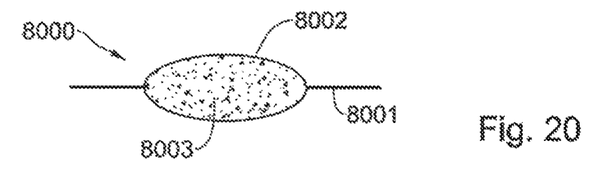
FIG. 20 is a schematic view of one compartment or several connected compartments of an orally administrable device according to the invention, showing the connector element made of said external biodegradable film or any absorbable medical suture.

FIG. 20 is a schematic view of one compartment (8000) of an orally administrable device according to the invention, which forms a connector element (8001) made of said external biodegradable film (8002) (in some embodiments said connector may be a absorbable medical suture) at the expanded form where the expandable-film is swelled after contact with gastric fluids. The gel matrix is formed within the compartment (8003), expanding said compartment.

Figure 21:
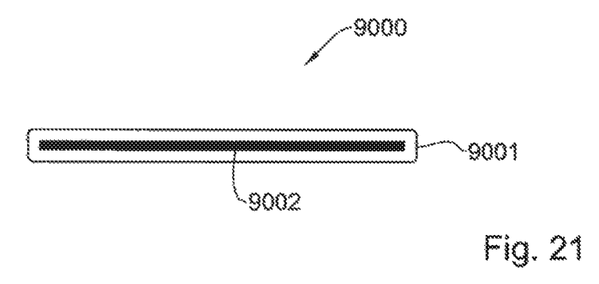
FIG. 21 is a schematic cross-section view of one compartment at the non-expanded form having an external biodegradable film enclosing a composition (marked in bold) composed of at least one gel-film and/or at least one combination of gel-gas film.
Figure 22:
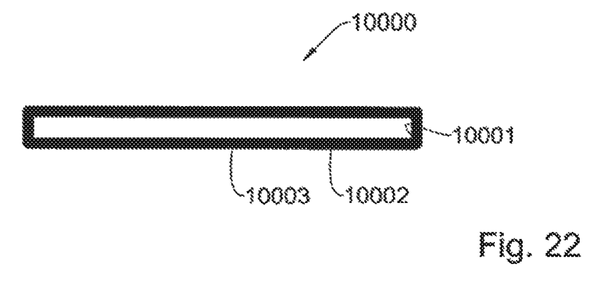
FIG. 22 is a schematic cross-section view of one compartment at the non-expanded form having at least one expandable multilayered biodegradable film comprising: at least one layer of external biodegradable film, and at least one expandable layer formed of gel-film and/or combination of gel-gas film.

The construction of the compartment at the non-expanded form is illustrated in FIG. 21 where a cross-section view describes one compartment (9000) at the non-expanded form having an external biodegradable film (9001) enclosing a composition (9002) composed of at least one gel-film and/or at least one combination of gel-gas film. FIG. 22 where a cross-section view describes one compartment (10000) at the non-expanded form having an expandable multilayered biodegradable film (10001) comprising: at least one layer of external biodegradable film (10002), and an expandable layer formed of gel-film and/or combination of gel-gas film (10003).

The invention claimed is:

1. A folded expandable gastro-retentive device having an initial folded form, said form being transformable, in sequence, upon delivery to a subject gastrointestinal system, into (a) an expanded 3-dimensional form, (b) a declined form, and (c) a disintegrated form,
  said device comprising at least one compartment having an external enteric-biodegradable film that allows stomach liquid permeation therethrough, said at least one compartment enclosing a film that comprises at least one gel-forming compound;
  wherein said at least one gel-forming compound is configured to undergo swelling into a gel upon contact with liquid in the stomach to transform said device into the expanded, 3-dimensional form (a);
  wherein said at least one gel-forming compound is configured to, upon continued stomach residence, undergo at least partial degradation thereby causing the device in the expanded form (a) to adopt the declined form (b) and evacuate through the pylorus into the intestine; and
  wherein the external enteric biodegradable film is configured to enterically degrade in the intestine to transform the device to the disintegrated form (c).

2. The device according to claim 1, wherein said liquid is stomach fluids.

3. The device according to claim 1, wherein said continued stomach residence lasts between about 0.5 hrs to about 12 hrs.

4. The device according to claim 1, wherein said film comprising the at least one gel-forming compound is a multilayered film.

5. The device according to claim 1, wherein enteric degradation of said external enteric-biodegradable film causes reduction in at least one of tensile strength and elasticity of said external enteric-biodegradable film.

6. The device according to claim 1, wherein said external enteric-biodegradable film has a thickness between about 3 and about 60 microns.

7. The device according to claim 1, wherein said external enteric-biodegradable film comprises at least one mechanical or chemically formed aperture permitting liquid penetration therethrough.

8. The device according to claim 1, wherein said at least one gel-forming compound is selected from gelatin, alginate, chitosan, dextran, collagen, hyaluronic acid, polyglutamic acid, elastin, calcium polycarbophil, acrylamides, styrene maleic anhydride, polyethylene oxide, polyacrylic acid, polyethylene glycol, carboxymethylcellulose, polyvinyl pyrrolidone, sodium polyacrylate, hydroxypropylmethylcellulose, poly glutamic acid (PGA), polyacrylamide, alginic acid, pullulan, starch, and any combination thereof.

9. The device according to claim 1, wherein said at least one gel-forming compound is a charged gel-forming compound.

10. The device according to claim 9, wherein said at least one charged gel-forming compound is at least one super absorbent polymer.

11. The device according to claim 1, being encased within a gastric degradable swallowable capsule.

12. The device according to claim 11, wherein the capsule is configured to expose in the initial folded form to stomach fluids.

13. The device according to claim 1, wherein said film that comprises the at least one gel-forming compound has a thickness of about 400 microns, about 500 microns, about 600 microns, about 700 microns, or about 800 microns.

14. The device according to claim 1, wherein said film that comprises the at least one gel-forming compound has a thickness of between about 5 microns and about 500 microns.

15. The device according to claim 1, wherein said film that comprises the at least one gel-forming compound has a thickness of less than 1500 microns.

16. The device according to claim 1, wherein said at least one gel-forming compound has a swelling ratio of about 10 to about 100.

17. The device according to claim 1, wherein said at least one compartment comprises at least two compartments connected to each other.

18. The device according to claim 17, wherein said at least two compartments form a closed ring 3-dimensional shape when the at least two compartments are connected to one to the other.

19. The device according to claim 18, wherein, in the expanded form (a), said closed ring 3-dimensional shape is a polygon.

20. The device according to claim 19, wherein said polygon is a triangle, a square, a pentagon, or a hexagon.

\* \* \* \* \*